United States Patent
Wu et al.

(10) Patent No.: US 11,034,763 B2
(45) Date of Patent: Jun. 15, 2021

(54) FLAG TAGGED CD19-CAR-T CELLS

(71) Applicants: ProMab Biotechnologies, Inc., Richmond, CA (US); Forevertek Biotechnology Co., Ltd., Hunan (CN)

(72) Inventors: Lijun Wu, Albany, CA (US); Vita Golubovskaya, Richmond, CA (US); Martyn Lewis, Danville, CA (US); Hua Zhou, Hercules, CA (US)

(73) Assignees: ProMab Biotechnologies, Inc., Richmond, CA (US); Forevertek Biotechnology Co., Ltd., Hunan (CN)

( * ) Notice: Subject to any disclaimer, the term of this patent is extended or adjusted under 35 U.S.C. 154(b) by 152 days.

(21) Appl. No.: 16/148,806

(22) Filed: Oct. 1, 2018

(65) Prior Publication Data

US 2019/0062430 A1 Feb. 28, 2019

Related U.S. Application Data

(63) Continuation of application No. PCT/US2017/024800, filed on Mar. 29, 2017.

(60) Provisional application No. 62/317,160, filed on Apr. 1, 2016.

(51) Int. Cl.

| A61P 35/00 | (2006.01) |
|---|---|
| C07K 16/30 | (2006.01) |
| C07K 16/28 | (2006.01) |
| A61K 35/17 | (2015.01) |
| C07K 14/725 | (2006.01) |
| C07K 14/705 | (2006.01) |
| C12N 5/0783 | (2010.01) |
| A61K 39/00 | (2006.01) |

(52) U.S. Cl.
CPC .......... C07K 16/2803 (2013.01); A61K 35/17 (2013.01); A61P 35/00 (2018.01); C07K 14/7051 (2013.01); C07K 14/70521 (2013.01); C07K 16/30 (2013.01); C12N 5/0636 (2013.01); *A61K 2039/505* (2013.01); *C07K 2317/56* (2013.01); *C07K 2317/622* (2013.01); *C07K 2317/73* (2013.01); *C07K 2319/03* (2013.01); *C07K 2319/30* (2013.01); *C07K 2319/33* (2013.01); *C07K 2319/43* (2013.01)

(58) Field of Classification Search
CPC ............ C07K 16/2803; C07K 14/7051; C07K 14/70521; C07K 16/30; A61P 35/00
USPC ........................................................ 424/133.1
See application file for complete search history.

(56) References Cited

U.S. PATENT DOCUMENTS

2012/0301447 A1 11/2012 Jensen

FOREIGN PATENT DOCUMENTS

| WO | 2015/095895 A1 | 6/2015 |
| WO | 2015/105522 A1 | 7/2015 |

OTHER PUBLICATIONS

Kochenderfer, James N., et al, "Construction and Pre-clinical Evaluation of an Anti-CD19 Chimeric Antigen Receptor", Journal of Immunotherapy, Sep. 2009, vol. 32, No. 7, pp. 689-702.
Jensen, Michael C., et al, "Design and implementation of adoptive therapy with chimeric antigen receptor-modified T cells", Immunol Rev., Author Manuscript, Jan. 2014, 257 (1): 127-144, pp. 1-32.
Liu, Lingfeng, et al, "Inclusion of Strep-tag II in design of antigen receptors for T-cell immunotherapy", Nature Biotechnology, Feb. 22, 2016, pp. 1-7.
Brudno, Jennifer N., et al, "Toxicities of chimeric antigen receptor T cells: recognition and management", Blood, Jun. 30, 2016, vol. 127, No. 26, pp. 3321-3330.
Rodino-Klapac, Louise R., et al, "Persistent Expression of FLAG-tagged Micro-dystrophin in Nonhuman Primates Following Intramuscular and Vascular Delivery", Molecular Therapy, Jan. 2010, vol. 18, No. 1, pp. 109-117.
Maude, Shannon L., et al, "Managing Cytokine Release Syndrome Associated With Novel T Cell-Engaging Therapies", Cancer J., 2014, 20(2): 119-122.
International Search Report dated Jul. 10, 2017 issued in PCT/US17/024800.

*Primary Examiner* — Yan Xiao
(74) *Attorney, Agent, or Firm* — Perkins Coie LLP; Viola T. Kung

(57) ABSTRACT

The present invention provides chimeric antigen receptor (CAR)-T cells modified to express a CAR fusion protein comprising from N-terminus to C-terminus: (i) a single-chain variable fragment (scFv) comprising $V_H$ and $V_L$, wherein scFv has an activity against a tumor antigen CD19, (ii) a transmembrane domain, (iii) at least one co-stimulatory domains, and (iv) an activating domain; wherein the fusion protein further comprises a FLAG tag N-terminus to scFv, C-terminus to scFv, or between $V_H$ and $V_L$. Using CD19-FLAG CAR-T cells instead of CD19 CAR-T cells, cytokine levels (Interferon-γ, IL-2 and IL6) caused by infused CAR-T cells are reduced.

8 Claims, 9 Drawing Sheets

Specification includes a Sequence Listing.

A

B

SEQUENCE LISTING

```
<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: synthetic

<400> SEQUENCE: 1

Asp Tyr Lys Asp Asp Asp Asp Lys
1               5

<210> SEQ ID NO 2
<211> LENGTH: 22
<212> TYPE: PRT
<213> ORGANISM: Homo sapiens

<400> SEQUENCE: 2

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 3
<211> LENGTH: 109
<212> TYPE: PRT
<213> ORGANISM: Mus musculus

<400> SEQUENCE: 3

Asp Ile Gln Met Glu Thr Thr Gln Thr Thr Ser Ser Leu Ser Ala Ser
1               5                   10                  15

Leu Gly Asp Arg Val Thr Ile Ser Cys Arg Ala Ser Gln Asp Ile Ser
            20                  25                  30

Lys Tyr Leu Asn Trp Tyr Gln Gln Lys Pro Asp Gly Thr Val Lys Leu
        35                  40                  45

Leu Ile Tyr His Thr Ser Arg Leu His Ser Gly Val Pro Ser Arg Phe
    50                  55                  60

Ser Gly Ser Gly Ser Gly Thr Asp Tyr Ser Leu Thr Ile Ser Asn Leu
65                  70                  75                  80

Glu Gln Glu Asp Ile Ala Thr Tyr Phe Cys Gln Gln Gly Asn Thr Leu
                85                  90                  95

Pro Tyr Thr Phe Gly Gly Gly Thr Lys Leu Glu Ile Thr
            100                 105

<210> SEQ ID NO 4
<211> LENGTH: 18
<212> TYPE: PRT
<213> ORGANISM: Artificial Sequence
<220> FEATURE:
<223> OTHER INFORMATION: synthetic

<400> SEQUENCE: 4
```

Gly Ser Thr Ser Gly Ser Gly Lys Pro Gly Ser Gly Glu Gly Ser Thr
1               5                   10                  15

Lys Gly

<210> SEQ ID NO 5
<211> LENGTH: 124
<212> TYPE: PRT
<213> ORGANISM: Mus musculus

<400> SEQUENCE: 5

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
            35                  40                  45

Gly Val Ile Trp Gly Ser Glu Thr Thr Tyr Tyr Asn Ser Ala Leu Lys
        50                  55                  60

Ser Arg Leu Thr Ile Ile Lys Asp Asn Ser Lys Ser Gln Val Phe Leu
65                  70                  75                  80

Lys Met Glu Thr Asn Ser Leu Gln Thr Asp Asp Thr Ala Ile Tyr Tyr
                85                  90                  95

Cys Ala Lys His Tyr Tyr Tyr Gly Gly Ser Tyr Ala Met Glu Thr Asp
                100                 105                 110

Tyr Trp Gly Gln Gly Thr Ser Val Thr Val Ser Ser
            115                 120

<210> SEQ ID NO 6
<211> LENGTH: 39
<212> TYPE: PRT
<213> ORGANISM: Homo sapiens

<400> SEQUENCE: 6

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
                20                  25                  30

Phe Pro Gly Pro Ser Lys Pro
            35

<210> SEQ ID NO 7
<211> LENGTH: 27
<212> TYPE: PRT
<213> ORGANISM: Homo sapiens

<400> SEQUENCE: 7

Phe Trp Val Leu Val Val Val Gly Gly Val Leu Ala Cys Tyr Ser Leu
1               5                   10                  15

Leu Val Thr Val Ala Phe Ile Ile Phe Trp Val
                20                  25

<210> SEQ ID NO 8
<211> LENGTH: 41
<212> TYPE: PRT
<213> ORGANISM: Homo sapiens

<400> SEQUENCE: 8

Arg Ser Lys Arg Ser Arg Leu Leu His Ser Asp Tyr Met Asn Met Thr
1               5                   10                  15

```
Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 9
<211> LENGTH: 112
<212> TYPE: PRT
<213> ORGANISM: Homo sapiens

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 519
<212> TYPE: PRT
<213> ORGANISM: Homo sapiens

<400> SEQUENCE: 10

Met Glu Thr Leu Leu Leu Val Thr Ser Leu Leu Leu Cys Glu Leu Pro
1               5                   10                  15

His Pro Ala Phe Leu Leu Ile Pro Asp Ile Gln Met Glu Thr Thr Gln
            20                  25                  30

Thr Thr Ser Ser Leu Ser Ala Ser Leu Gly Asp Arg Val Thr Ile Ser
        35                  40                  45

Cys Arg Ala Ser Gln Asp Ile Ser Lys Tyr Leu Asn Trp Tyr Gln Gln
    50                  55                  60

Lys Pro Asp Gly Thr Val Lys Leu Leu Ile Tyr His Thr Ser Arg Leu
65                  70                  75                  80

His Ser Gly Val Pro Ser Arg Phe Ser Gly Ser Gly Ser Gly Thr Asp
                85                  90                  95

Tyr Ser Leu Thr Ile Ser Asn Leu Glu Gln Glu Asp Ile Ala Thr Tyr
            100                 105                 110

Phe Cys Gln Gln Gly Asn Thr Leu Pro Tyr Thr Phe Gly Gly Gly Thr
        115                 120                 125

Lys Leu Glu Ile Thr Gly Ser Thr Ser Gly Ser Gly Lys Pro Gly Ser
    130                 135                 140

Gly Glu Gly Ser Thr Lys Gly Glu Val Lys Leu Gln Glu Ser Gly Pro
145                 150                 155                 160

Gly Leu Val Ala Pro Ser Gln Ser Leu Ser Val Thr Cys Thr Val Ser
                165                 170                 175

Gly Val Ser Leu Pro Asp Tyr Gly Val Ser Trp Ile Arg Gln Pro Pro
            180                 185                 190
```

```
Arg Lys Gly Leu Glu Trp Leu Gly Val Ile Trp Gly Ser Glu Thr Thr
            195                 200                 205

Tyr Tyr Asn Ser Ala Leu Lys Ser Arg Leu Thr Ile Ile Lys Asp Asn
    210                 215                 220

Ser Lys Ser Gln Val Phe Leu Lys Met Glu Thr Asn Ser Leu Gln Thr
225                 230                 235                 240

Asp Asp Thr Ala Ile Tyr Tyr Cys Ala Lys His Tyr Tyr Gly Gly
            245                 250                 255

Ser Tyr Ala Met Glu Thr Asp Tyr Trp Gly Gln Gly Thr Ser Val Thr
            260                 265                 270

Val Ser Ser Ala Ala Asp Tyr Lys Asp Asp Asp Lys Ile Glu
        275                 280                 285

Val Met Glu Thr Tyr Pro Pro Pro Tyr Leu Asp Asn Glu Lys Ser Asn
        290                 295                 300

Gly Thr Ile Ile His Val Lys Gly Lys His Leu Cys Pro Ser Pro Leu
305                 310                 315                 320

Phe Pro Gly Pro Ser Lys Pro Phe Trp Val Leu Val Val Gly Gly
            325                 330                 335

Val Leu Ala Cys Tyr Ser Leu Leu Val Thr Val Ala Phe Ile Ile Phe
            340                 345                 350

Trp Val Arg Ser Lys Arg Ser Arg Leu Leu His Ser Asp Tyr Met Glu
            355                 360                 365

Thr Asn Met Glu Thr Thr Pro Arg Arg Pro Gly Pro Thr Arg Lys His
    370                 375                 380

Tyr Gln Pro Tyr Ala Pro Pro Arg Asp Phe Ala Ala Tyr Arg Ser Arg
385                 390                 395                 400

Val Lys Phe Ser Arg Ser Ala Asp Ala Pro Ala Tyr Gln Gln Gly Gln
            405                 410                 415

Asn Gln Leu Tyr Asn Glu Leu Asn Leu Gly Arg Arg Glu Glu Tyr Asp
            420                 425                 430

Val Leu Asp Lys Arg Arg Gly Arg Asp Pro Glu Met Glu Thr Gly Gly
            435                 440                 445

Lys Pro Arg Arg Lys Asn Pro Gln Glu Gly Leu Tyr Asn Glu Leu Gln
    450                 455                 460

Lys Asp Lys Met Glu Thr Ala Glu Ala Tyr Ser Glu Ile Gly Met Glu
465                 470                 475                 480

Thr Lys Gly Glu Arg Arg Gly Lys Gly His Asp Gly Leu Tyr Gln
            485                 490                 495

Gly Leu Ser Thr Ala Thr Lys Asp Thr Tyr Asp Ala Leu His Met Glu
            500                 505                 510

Thr Gln Ala Leu Pro Pro Arg
            515
```

FLAG TAGGED CD19-CAR-T CELLS

This application is a continuation of PCT/US2017/024800, filed Mar. 29, 2017; which claims the priority of U.S. Provisional Application No. 62/317,160, filed Apr. 1, 2016. The contents of the above-identified applications are incorporated herein by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Mar. 27, 2017, and a size of 9.6 kilobytes. The Sequence Listing filed via EFS-Web is part of the specification and is hereby incorporated in its entirety by reference herein.

FIELD OF THE INVENTION

The present invention relates to a chimeric antigen receptor and T cells expressing the chimeric antigen receptor, which are useful in the field of adoptive immunity gene therapy for tumors. The invention particularly relates to FLAG-tagged CD19-CAR-T cells.

BACKGROUND OF THE INVENTION

Immunotherapy is emerging as a highly promising approach for the treatment of cancer. T cells or T lymphocytes are the armed forces of our immune system that constantly look for foreign antigens and discriminates abnormal (cancer or infected cells) from normal cells. Genetically modifying T cells with CARs are a common approach to design tumor-specific T cells. CAR-T cells targeting tumor-associated antigens can be infused into patients (called adoptive T cell therapy) representing an efficient immunotherapy approach. The advantage of CAR-T technology compared with chemotherapy or antibody is that reprogrammed engineered T cells can proliferate and persist in the patient and work like a living drug.

CARs (Chimeric antigen receptors) usually consist of a monoclonal antibody-derived single-chain variable fragment (scFv) linked by a hinge and transmembrane domain to a variable number of intracellular signaling domains and a single, cellular activating, CD3-zeta domain.

FIG. 1 shows the evolution of CARs from first generation (left, with no co-stimulation domains) to second generation (middle, with one co-stimulation domain CD28 or 4-BB) to third generation (with two or several co-stimulation domains), see Golubovskaya, Wu, Cancers, 2016 Mar. 15; 8(3). Generating CARs with multiple costimulatory domains (third generation CAR) have led to increased cytolytic activity, and significantly improved persistence of CAR-T cells that demonstrate augmented antitumor activity.

Chimeric antigen receptor (CAR) T cells can produce durable remissions in hematologic malignancies that are not responsive to standard therapies. Yet the use of CAR T cells is limited by potentially severe toxicities. Early case reports of unexpected organ damage and deaths following CAR T-cell therapy first highlighted the possible dangers of this new treatment. CAR T cells can potentially damage normal tissues by specifically targeting a tumor-associated antigen that is also expressed on those tissues. Cytokine release syndrome (CRS), a systemic inflammatory response caused by cytokines released by infused CAR T cells can lead to widespread reversible organ dysfunction. CRS is the most common type of toxicity caused by CAR T cells. (Blood. 2016; 127(26): 3321-3330) In CRS, a systemic inflammatory response that can lead to death if untreated (Bonifant, et al, 2016, Mol Ther Oncolytics 3, 16011). CRS patient experiences fever, hypotension, hypoxia, and neurologic disorders that may require aggressive medical support (Davila, et al, 2014, Sci Transl Med 6, 224ra225).

There exists a need for an improved adoptive T cell immunotherapy with reduced toxicities because reduction of CRS is very important for clinic to decrease adverse effects.

DETAILED DESCRIPTION OF THE INVENTION

Definitions

Figure 1:
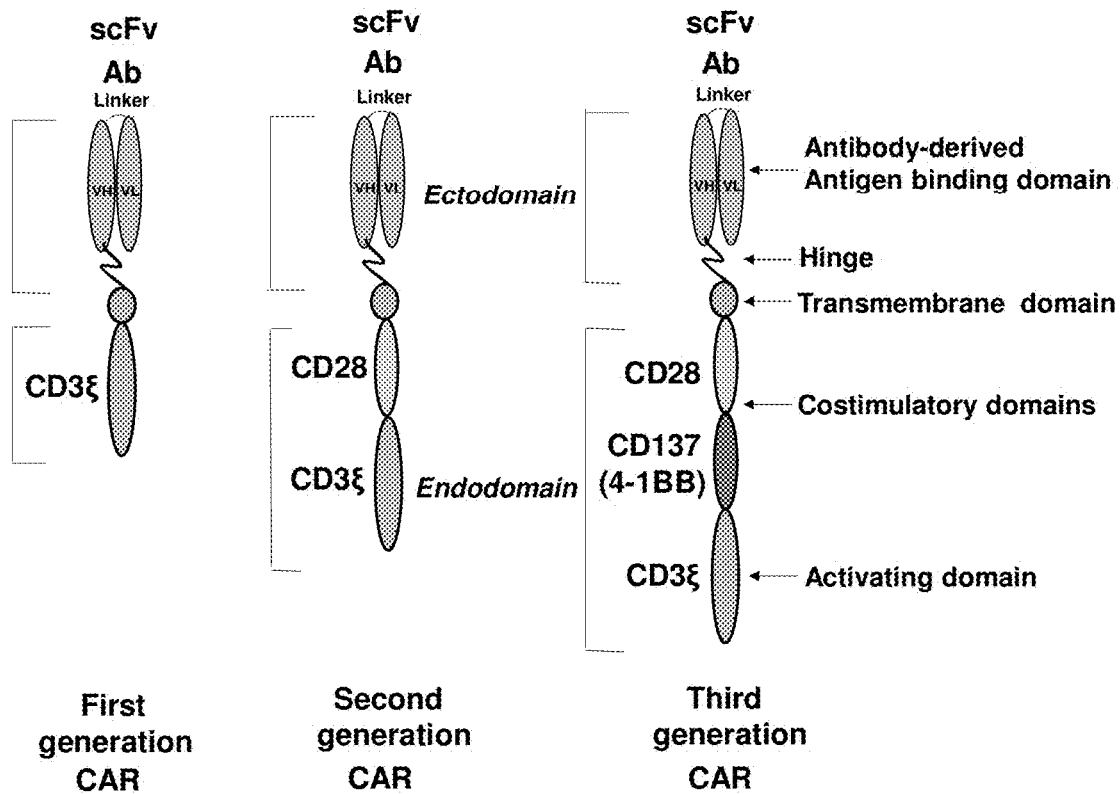
FIG. 1 shows the structure of CAR from first to third generation.

As used herein, "adoptive cell therapy" (ACT) is a treatment that uses a cancer patient's own T lymphocytes with anti-tumor activity, expanded in vitro and reinfused into the patient with cancer.

As used herein, "affinity" is the strength of binding of a single molecule to its ligand. Affinity is typically measured and reported by the equilibrium dissociation constant ($K_D$ or Kd), which is used to evaluate and rank order strengths of bimolecular interactions.

As used herein, a "chimeric antigen receptor (CAR)" means a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, a "domain" means one region in a polypeptide which is folded into a particular structure independently of other regions.

As used herein, a FLAG-tag, or FLAG octapeptide, or FLAG epitope, is a polypeptide protein tag that can be added to a protein using recombinant DNA technology, having the sequence motif DYKDDDDK (SEQ ID NO: 1). It can be fused to the C-terminus or the N-terminus of a protein, or inserted within a protein.

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for preparing an scFv are known to a person skilled in the art.

As used herein, a "tumor antigen" means a biological molecule having antigenecity, expression of which causes cancer.

Description

The inventors have discovered that by adding a FLAG sequence in CD19 CAR construct, CD19-FLAG CAR-T cells produced less IFN-γ, IL-2 and IL6 than did the CD19 CAR-T cells, which indicates that CD19-FLAG CAR-T cells can be less toxic and safer than the corresponding CD19-CAR-T cells. The inventors thus have discovered an improved adoptive T cell therapy (ACT) with reduced toxicities. By using FLAG-tagged CAR-T cells in ACT, a subject has reduced levels of released cytokines and thus has reduced incidence of cytokine release syndrome (CRS) comparing with a subject administered with similar CAR-T cells but without a FLAG tag in CAR.

The present invention is directed to an adoptive cell therapy method for treating cancer, comprising the step of administering CD19-FLAG CAR-T cells to a subject suffering from cancer, whereby the subject has reduced cytokine release caused by infused CAR T cells comparing with a subject administered with similar CAR-T cells but without a FLAG tag in CAR.

The present invention is also directed to an adoptive cell therapy method for treating cancer comprising the step of administering CD19-FLAG CAR-T cells to a subject suffering from cancer, whereby the subject has reduced incidence of cytokine release syndrome comparing with a subject administered with similar CAR-T cells but without a FLAG tag in CAR.

The present invention provides a chimeric antigen receptor fusion protein comprising from N-terminus to C-terminus: (i) a single-chain variable fragment (scFv) having activity against a tumor antigen, (ii) a transmembrane domain, (iii) at least one co-stimulatory domain having one or more binding motif immediately repeated at least one time, and (iv) an activating domain; wherein the fusion protein further comprises a FLAG tag located C-terminus to scFv, C-terminus to scFv, or between the $V_H$ and $V_L$ of scFc.

In one embodiment, the tumor antigen is selected from the group consisting of: CD19, CD20, BCMA, CD22, CD38, CD138, mesothelin, VEGFR-2, CD4, CD5, CD30, CD22, CD24, CD25, CD28, CD30, CD33, CD47, CD52, CD56, CD80, CD81, CD86, CD123, CD171, CD276, B7H4, CD133, EGFR, GPC3; PMSA, CD3, CEACAM6, c-Met, EGFRvIII, ErbB2/HER-2, ErbB3/HER3, ErbB4/HER-4, EphA2,10a, IGF1R, GD2, O-acetyl GD2, O-acetyl GD3, GHRHR, GHR, FLT1, KDR, FLT4, CD44v6, CD151, CA125, CEA, CTLA-4, GITR, BTLA, TGFBR2, TGFBR1, IL6R, gp130, Lewis A, Lewis Y, NGFR, MCAM, TNFR1, TNFR2, PD1, PD-L1, PD-L2, HVEM, MAGE-A, NY-ESO-1, PSMA, RANK, ROR1, ROR-2, TNFRSF4, CD40, CD137, TWEAK-R, LTPR, LIFRP, LRP5, MUC1, TCRa, TCRp, TLR7, TLR9, PTCH1, WT-1, Robol, a, Frizzled, OX40, CD79b, and Notch-1-4. Preferred tumor antigens are CD19, CD20, BCMA, CD22, CD38, and CD138.

In one embodiment, the tumor antigen is human cluster of differentiation 19 (CD19), which is a protein encoded by the CD19 gene, and is a B-lymphocyte antigen found on the surface of B-cells.

The CAR of the present invention comprises a single chain variable fragment (scFv) that binds specifically to the tumor antigen of interest. The heavy chain (H chain) and light chain (L chain) fragments of an antibody are linked via a linker sequence. For example, a linker can be 5-20 amino acids. The scFv structure can be VL-linker-VH, or VH-linker-VL, from N-terminus to C-terminus.

The CAR of the present invention comprises a transmembrane domain which spans the membrane. The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor α or β chain, a CD3 zeta chain, CD28, CD3-epsilon, CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. It is preferable that a triplet of phenylalanine, tryptophan and valine is found at each end of the synthetic transmembrane domain. In preferred embodiments, the transmembrane domain is derived from CD28 or CD8, which give good receptor stability.

In the present invention, the co-stimulatory domain is selected from the group consisting of human CD28, 4-1BB (CD137), ICOS-1, CD27, OX 40 (CD137), DAP10, and GITR (AITR).

The endodomain (the activating domain) is the signal-transmission portion of the CAR. After antigen recognition, receptors cluster and a signal is transmitted to the cell. The most commonly used endodomain component is that of CD3-zeta (CD3 Z or CD3), which contains 3 ITAMs. This transmits an activation signal to the T cell after antigen is bound. CD3-zeta may not provide a fully competent activation signal and additional co-stimulatory signaling may be needed. For example, one or more co-stimulating domains can be used with CD3-Zeta to transmit a proliferative/survival signal.

The CAR fusion protein further comprises a FLAG tag located at N-terminus to scFv, or C-terminus to scFv, or between $V_H$ and $V_L$. The FLAG tag needs to be in extracellular domain, and not in the intracellular domain. In addition to FLAG tag, other tags may be used in the construct; however, FLAG tag is preferred because it does not cause immunogenicity and has decreased level of cytokine secretion.

The CAR of the present invention may comprise a signal peptide N-terminal to the ScFv so that when the CAR is expressed inside a cell, such as a T-cell, the nascent protein is directed to the endoplasmic reticulum and subsequently to the cell surface, where it is expressed. The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases. As an example, the signal peptide may derive from human CD8 or GM-CSF, or a variant thereof having 1 or 2 amino acid mutations provided that the signal peptide still functions to cause cell surface expression of the CAR.

The CAR of the present invention may comprise a spacer sequence as a hinge to connect scFv with the transmembrane domain and spatially separate antigen binding domain from the endodomain. A flexible spacer allows to the binding domain to orient in different directions to enable its binding to a tumor antigen. The spacer sequence may, for example, comprise an IgG1 Fc region, an IgG1 hinge or a CD8 stalk, or a combination thereof. A human CD28 or CD8 stalk is preferred.

Figure 2:
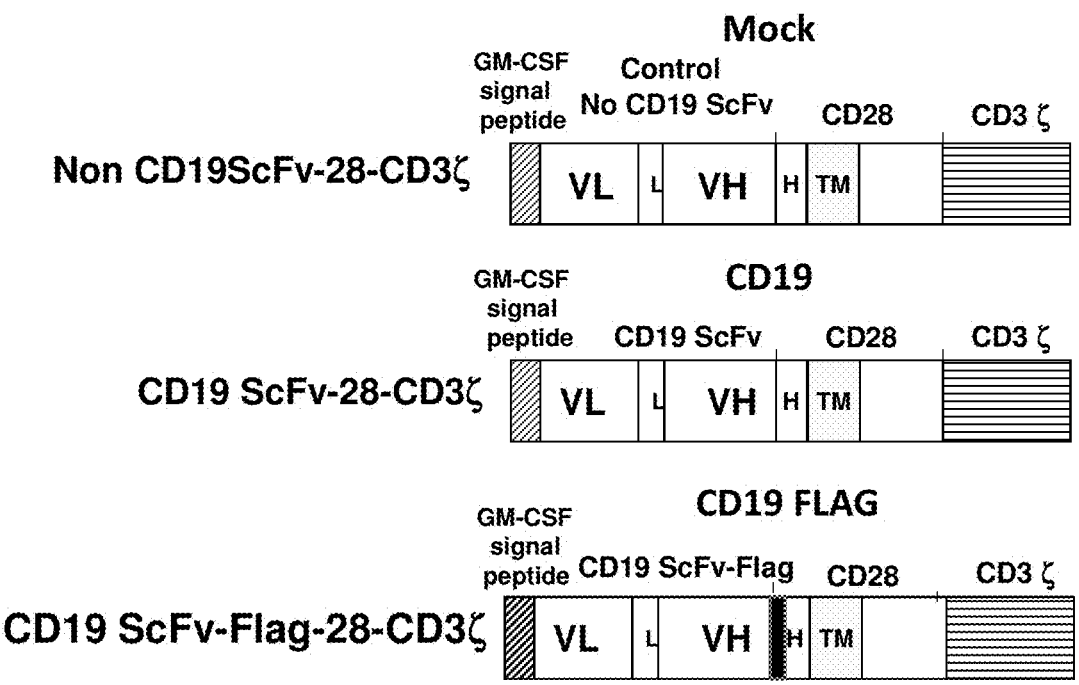
FIG. 2 shows the structures of Non-CD19, CD19, and CD19 Flag CAR constructs. Abbreviation: L, linker; H, hinge region from CD28; TM, transmembrane domain from CD28; F, FLAG epitope.

FIG. 2 shows the structures of Non CD19 ScFv-28-CDζ3, CD19 ScFv-28-CD3ζ, and CD19 ScFvFlag-28-CD3ζ. CM-CSF signal peptide, anti-CD19 scFv and CD28 co-stimulating domain are illustrated in the construct. FLAG tag is illustrated after anti-CD19 scFv in FIG. 2, but FLAG can also be introduced N-terminal to scFv, or in between VL and VH.

The present invention provides a nucleic acid encoding the CAR described above. The nucleic acid encoding the CAR can be prepared from an amino acid sequence of the specified CAR by a conventional method. A base sequence encoding an amino acid sequence can be obtained from the aforementioned NCBI RefSeq IDs or accession numbers of GenBenk for an amino acid sequence of each domain, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

The nucleic acid encoding the CAR of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a Sendai virus vector, an Epstein-Barr virus (EBV) vector, and a HSV vector can be used. As the virus vector, a virus vector lacking the replicating ability so as not to self-replicate in an infected cell is preferably used.

For example, when a retrovirus vector is used, the process of the present invention can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+en-vAm-12, and Psi-Crip. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

The present invention provides T cells modified to express the chimeric antigen receptor fusion protein as described above. CAR-T cells of the present invention bind to a specific antigen via the CAR, thereby a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, or the like as an index.

T cells modified to express the CAR can be used as a therapeutic agent for a disease. The therapeutic agent comprises the T cells expressing the CAR as an active ingredient, and may further comprise a suitable excipient. Examples of the excipient include pharmaceutically acceptable excipients known to a person skilled in the art.

The inventors have demonstrated that FLAG-tagged CD19-specific CAR-T cells are highly effective in vitro and in vivo. In vitro, CD19-FLAG CAR-T cells expand over 100-fold, had a >70% transduction efficiency and are highly cytotoxic against $CD19^+$ but not $CD19^-$ cells. In vivo, CD19-FLAG CAR-T cells exhibit substantial anti-tumor activity against both $CD19^+$ solid tumors and $CD19^+$ hematological tumors. Efficacy in vivo is associated with CAR-T cell expansion, tumor cell apoptosis and increased animal survival. These results demonstrate the strong efficacy of FLAG-tagged CD19 CAR-T cells in solid and hematological cancer models and suggest that FLAG-tagged CAR-T cells are useful in the treatment of human malignancies.

The inventors have discovered that although CD19-FLAG CAR-T cells are as cytotoxic as non-tagged CD19 CAR-T cells in vitro, CD19-FLAG CAR-T cells produce less IFN-γ, IL-2, and Il-6 than the CD19 CAR-T cells. This result suggests that CD19-FLAG CAR-T cells are less toxic than CD19 CAR-T cells in vivo, as high levels of cytokine secretion by CAR-T cells in patients often lead to cytokine release syndrome (CRS).

Decreasing cytokine levels by using CD19-FLAG CAR-T cells instead of CD19 CAR-T cells are advantageous in the clinic due to a decreased incidence of CRS. The decreased cytokine production of CD19-FLAG CAR-T cells may allow multiple applications.

The use of CD19-FLAG CAR-T cells confers other benefits, as the FLAG tag can be used in the clinic for imaging the CAR-T cells after application, or beforehand for CAR-T cell sorting, manufacturing or other applications. Importantly, the FLAG tag is not immunogenic in primates (Rodino-Klapac, et al, 2010, Mol Ther 18, 109-117), and thus the use of CD19-FLAG CAR-T cells does not cause an adverse immune response in a subject due to the FLAG tag.

The following examples further illustrate the present invention. These examples are intended merely to be illustrative of the present invention and are not to be construed as being limiting.

EXAMPLES

Materials and Methods

Example 1

Cell Lines

We generated a novel solid tumor xenograft model using cervical cancer HeLa cells overexpressing CD19 in immunodeficient mice. This model allows us to study hematological cancer targets in the context of a solid tumor microenvironment and its associated inhibitory factors, such as immune checkpoint pathways (PD-1, CTLA-4, LAG-3), angiogenesis/vasculogenesis, hypoxia and Treg cells. For example, PD-1 inhibition was recently shown to increase CAR-T cell efficacy (Devaud et al, 2013, Clin Cancer Res 19, 5636-5646).

HeLa cervical carcinoma cells were purchased from the ATCC (Manassas, Va.) and cultured in DMEM (GE Healthcare, Chicago, Ill.) containing 10% FBS (AmCell, Mountain View, Calif.). Raji Burkitt's lymphoma cells and K562 cells (CML leukemia) were purchased from the ATCC and cultured in RPMI-1640 medium (Thermo Fisher, Waltham, Mass.) containing 10% FBS. Human peripheral blood mononuclear cells (PBMC) were isolated by density sedimentation over Ficoll-Paque (GE Healthcare). HEK293FT cells were a gift from AlStem (Richmond, Calif.) and were cultured in DMEM containing 10% FBS. All cell lines were authenticated by flow cytometry in our laboratory, using cell-specific surface markers.

Example 2

CAR Constructs

The mouse FMC63 anti-CD19 scFv (Kochenderfer et al (2009), I. Immunother, 32: 689-702) was inserted into a second-generation CAR cassette containing a signaling peptide from GM-CSF, a hinge region, transmembrane domain and costimulatory domain from CD28, and the CD3 zeta activation domain; this CAR is herein called the CD19 CAR. The FLAG tag (DYKDDDDK, SEQ ID NO: 1) was inserted into the CD19 CAR between the scFv and hinge region; this CAR is herein called the CD19-FLAG CAR. An scFv specific for an intracellular protein was used instead of the FMC63 scFv; this CAR is herein called the mock CAR.

Example 3

Generation of CAR-Encoding Lentivirus

DNAs encoding the CARs were synthesized and subcloned into a third-generation lentiviral vector, Lenti CMV-MCS-EF1a-puro by Syno Biological (Beijing, China). All CAR lentiviral constructs were sequenced in both directions to confirm CAR sequence and used for lentivirus production. Ten million growth-arrested HEK293FT cells (Thermo Fisher) were seeded into T75 flasks and cultured overnight, then transfected with the pPACKH1 Lentivector Packaging mix (System Biosciences, Palo Alto, Calif.) and 10 μg of each lentiviral vector using the CalPhos Transfection Kit (Takara, Mountain View, Calif.). The next day the medium was replaced with fresh medium, and 48 h later the lentivirus-containing medium was collected. The medium was cleared of cell debris by centrifugation at 2100 g for 30 min. The virus particles were collected by centrifugation at 112,000 g for 100 min, suspended in AIM V medium, aliquoted and frozen at −80° C. The titers of the virus preparations were determined by quantitative RT-PCR using the Lenti-X qRT-PCR kit (Takara) according to the manufacturer's protocol and the 7900HT thermal cycler (Thermo Fisher). The lentiviral titers were $>1\times10^8$ pfu/ml.

Example 4

Generation and Expansion of CAR-T Cells

PBMC were suspended at $1\times10^6$ cells/ml in AIM V-AlbuMAX medium (Thermo Fisher) containing 10% FBS and 300 U/ml IL-2 (Thermo Fisher), mixed with an equal number (1:1 ratio) of CD3/CD28 Dynabeads (Thermo Fisher), and cultured in non-treated 24-well plates (0.5 ml per well). At 24 and 48 hours, lentivirus was added to the cultures at a multiplicity of infection (MOI) of 5, along with 1 µl of TransPlus transduction enhancer (AlStem). As the T cells proliferated over the next two weeks, the cells were counted every 2-3 days and fresh medium with 300 U/ml IL-2 was added to the cultures to maintain the cell density at $1\text{-}3\times10^6$ cells/ml.

Example 5

Flow Cytometry

To measure CAR expression, 0.5 million cells were suspended in 100 µl of buffer (PBS containing 0.5% BSA) and incubated on ice with 1 µl of human serum (Jackson Immunoresearch, West Grove, Pa.) for 10 min. Then 1 µl of allophycocyanin (APC)-labeled anti-CD3 (eBioscience, San Diego, Calif.), 2 µl of 7-aminoactinomycin D (7-AAD, BioLegend, San Diego, Calif.), and 2 µl of either phycoerythrin (PE)-labeled anti-FLAG or its isotype control PE rat IgG2a (both from BioLegend) was added, and the cells were incubated on ice for 30 min. The cells were rinsed with 3 ml of buffer, then suspended in buffer and acquired on a FACSCalibur (BD Biosciences). Cells were analyzed first for light scatter versus 7-AAD staining, then the 7-AAD⁻ live gated cells were plotted for CD3 staining versus FLAG staining or isotype control staining. For the mouse tumor studies, 100 µl of blood was stained at room temperature for 30 min with 1 µl of APC anti-CD3, 2 µl of fluorescein isothiocyanate (FITC)-labeled anti-CD8a (eBioscience), 2 µl of 7-AAD, and 2 µl of either PE anti-FLAG or PE rat IgG2a. Erythrocytes were lysed with 3.5 ml of RBC lysing solution (150 mM $NH_4Cl$, 10 mM $NaHCO_3$, 1 mM EDTA pH 8), then leukocytes were collected by centrifugation and rinsed with 2 ml of cold buffer before acquisition.

Example 6

Generation of the Stable HeLa-CD19 Cell Line

To generate HeLa cells stably expressing human CD19, a DNA encoding the human CD19 open reading frame was synthesized and subcloned into the pCD510 lentiviral vector (System Biosciences) by Syno Biological. Lentivirus containing the vector was made as described above. HeLa cells were infected with the lentivirus at an MOI of 5 and cultured in the presence of 1 µg/ml puromycin to generate resistant cells, herein called HeLa-CD19. The expression of CD19 was confirmed by flow cytometry with a CD19 antibody (BioLegend).

Example 7

Real-Time Cytotoxicity Assay (RTCA)

Adherent target cells (HeLa or HeLa-CD19) were seeded into 96-well E-plates (Acea Biosciences, San Diego, Calif.) at $1\times10^4$ cells per well and monitored in culture overnight with the impedance-based real-time cell analysis (RTCA) iCELLigence system (Acea Biosciences). The next day, the medium was removed and replaced with AIM V-AlbuMAX medium containing 10% FBS $\pm1\times10^5$ effector cells (CAR-T cells or non-transduced T cells), in triplicate. The cells in the E-plates were monitored for another 2-3 days with the RTCA system, and impedance was plotted over time. Cytolysis was calculated as (impedance of target cells without effector cells–impedance of target cells with effector cells)×100/impedance of target cells without effector cells. For non-adherent target cells (Raji), the E-plates were first coated with an anti-CD40 antibody (Acea Biosciences) to bind to the CD40⁺ Raji cells. Then $1\times10^4$ Raji cells were plated per well and the RTCA assay was performed as described above.

Example 8

Cytokine Induction Assay

The target cells (Raji, K562, HeLa or HeLa-CD19) were cultured with the effector cells (CAR-T cells or non-transduced T cells) at a 1:1 ratio ($1\times10^4$ cells each) in U-bottom 96-well plates with 200 µl of AIM V-AlbuMAX medium containing 10% FBS, in triplicate. After 16 h the top 150 µl of medium was transferred to V-bottom 96-well plates and centrifuged at 300 g for 5 min to pellet any residual cells. The top 120 µl of supernatant was transferred to a new 96-well plate and analyzed by ELISA for human IFN-γ and IL-2 levels using kits from Thermo Fisher according to the manufacturer's protocol.

Example 9

Mouse Tumor Studies

Six-week old male NSG mice (Jackson Laboratories, Bar Harbor, Me.) were housed and manipulated in strict accordance with the Institutional Animal Care and Use Committee (IACUC). Each mouse was injected subcutaneously on day 0 with 100 µl of $2\times10^6$ HeLa-CD19 cells in sterile PBS. In one study, CAR-T cells in PBS were injected intra-tumor on days 19 ($5\times10^6$ cells) and 33 ($9\times10^6$ cells), and tumor growth was analyzed. In another study, CAR-T cells were injected intravenously on days 8 and 14 ($1\times10^7$ cells each day). Tumor sizes were measured with calipers twice-weekly and tumor volume (in mm³) was determined using the formula $W^2L/2$, where W is tumor width and L is tumor length. Tumors were excised and fixed in 4% paraformaldehyde, then embedded in paraffin wax and stained by immunohistochemistry. At the end of the intravenous CAR-T cell study, 100 µl of blood was collected and stained with different antibodies by flow cytometry as indicated above. For the Raji tumor model, $5\times10^5$ luciferase-expressing Raji cells in 0.1 ml of PBS were injected intravenously, and the next day $5\times10^6$ CD19-FLAG CAR-T cells in 0.2 ml of PBS were injected intravenously. On days 6 and 14, the mice were imaged with the Xenogen IVIS Spectrum (PerkinElmer, Waltham, Mass.) system and tumor growth was monitored by measuring bioluminescence in photons per seconds.

Example 10

Immunohistochemistry (IHC)

Tumor tissue sections (4 µm) were deparaffinized in xylenes twice for 10 min, then hydrated in graded alcohols and rinsed in PBS. Antigen retrieval was performed for 20 min in a pressure cooker using 10 mM citrate buffer, pH 6.0. The sections were cooled, rinsed with PBS, incubated in a 3% $H_2O_2$ solution for 10 min, and rinsed with PBS. The tissue sections were incubated in goat serum for 20 min and then incubated with rabbit anti-cleaved caspase-3 (Asp175, Cell Signaling Technology, Danvers, Mass.) or rabbit IgG (Jackson Immunoresearch) at 0.2 µg/ml overnight at 4° C. The sections were rinsed with PBS, incubated with biotin-conjugated goat anti-rabbit IgG for 10 min, rinsed with PBS, incubated with streptavidin-conjugated peroxidase for 10 min, and rinsed with PBS. Finally, the sections were incubated in DAB substrate solution for 2-5 min, immersed in tap water, counterstained with hematoxylin, rinsed with water, and dehydrated in graded alcohols and xylenes. Coverslips were mounted with glycerin. All reagents except those noted were from MaiXin.BIO (Fuzhou, China). Images were acquired on a Motic DMB5-2231PL microscope with Images Plus 2.0 software (Motic, Xiamen, China). To quantitate cleaved caspase-3 staining, six random microscopic fields from each tumor were analyzed with ImageJ software (National Institutes of Health). Each image was split into an RGB stack, then the area of the blue stack above an arbitrary threshold (80) was measured.

Results

Statistical Analysis

Data were analyzed and plotted with Prism software (GraphPad, San Diego, Calif.). Comparisons between two groups were performed by unpaired Student's t test, and comparisons between three groups were performed by one-way ANOVA with Tukey's post-hoc test, except where noted.

Example 11

CAR Constructs

A human CD19-specific CAR was constructed consisting of the FMC63 murine single-chain variable fragment (scFv); hinge, transmembrane and co-stimulation domains from human CD28; and the activation domain of human CD3 zeta (FIG. 2). A "mock" CAR with an scFv specific for an intracellular protein—and thus not reactive with intact cells—was constructed in the same manner (FIG. 2). In addition, the 8-amino acid FLAG epitope was inserted between the scFv and hinge region of the CD19-specific CAR.

Example 12

Sequences of CAR Constructs

The amino acid sequences of each segment of CD19 CAR and CD19-FLAG CAR constructs used in our experiments are shown below. Each segment can be replaced with amino acid sequence with at least 95% identity.

<Human GM-CSF Signal peptide>
SEQ ID NO: 2
MLLLVTSLLLCELPHPAFLLIP

FMC63 anti-CD19 scFv ScFv (VL-Linker-VH)
<VL>
SEQ ID NO: 3
D I Q Met T Q T T S S L S A S L G D R V T I S C R
A S Q D I S K Y L N W Y Q Q K P D G T V K L L I Y
H T S R L H S G V P S R F S G S G S G T D Y S L T
I S N L E Q E D I A T Y F C Q Q G N T L P Y T F G
G G T K L E I T <linker>
SEQ ID NO: 4
G S T S G S G K P G S G E G S T K G <VH>
SEQ ID NO: 5
E V K L Q E S G P G L V A P S Q S L S V T C T V S
G V S L P D Y G V S W I R Q P P R K G L E W L G V
I W G S E T T Y Y N S A L K S R L T I I K D N S K
S Q V F L K Met N S L Q T D D T A I Y Y C A K H Y
Y Y G G S Y A Met D Y W G Q G T S V T V S S In our contruct, we have 3 amino acids AAA after VH.

<Flag tag> if present, after VH,
SEQ ID NO: 5
DYKDDDDK

<CD28 hinge>
SEQ ID NO: 6
I E V M Y P P P Y L D N E K S N G T I I H V K G K
H L C P S P L F P G P S K P <Transmembrane Domain TM28>
SEQ ID NO: 7
F W V L V V V G G V L A C Y S L L V T V A F I I F
W V <Co-stimulating domain CD28>
SEQ ID NO: 8
R S K R S R L L H S D Y M N M T P R R P G P T R K
H Y Q P Y A P P R D F A A Y R S <Activation domain CD3-zeta>
SEQ ID NO: 9
R V K F S R S A D A P A Y Q Q G Q N Q L Y N E L N
L G R R E E Y D V L D K R R G R D P E M G G K P R
R K N P Q E G L Y N E L Q K D K M A E A Y S E I G
M K G E R R R G K G H D G L Y Q G L S T A T K D T
Y D A L H M Q A L P P R CD19-FLAG CAR sequence can be shown as SEQ ID NO: 10, FLAG is bold and underlined
Met L L L V T S L L L C E L P H P A F L L I P D I
Q Met T Q T T S S L S A S L G D R V T I S C R A S
Q D I S K Y L N W Y Q Q K P D G T V K L L I Y H T
S R L H S G V P S R F S G S G S G T D Y S L T I S
N L E Q E D I A T Y F C Q Q G N T L P Y T F G G G
T K L E I T G S T S G S G K P G S G E G S T K G E
V K L Q E S G P G L V A P S Q S L S V T C T V S G
V S L P D Y G V S W I R Q P P R K G L E W L G V I
W G S E T T Y Y N S A L K S R L T I I K D N S K S
Q V F L K Met N S L Q T D D T A I Y Y C A K H Y Y
G G S Y A Met D Y W G Q G T S V T V S S A A A D
YKDDDDK I E V Met Y P P P Y L D N E K S N G T I I
H V K G K H L C P S P L F P G P S K P F W V L V V -continued

V G G V L A C Y S L L V T V A F I I F W V R S K R

S R L L H S D Y Met N Met T P R R P G P T R K H Y

Q P Y A P P R D F A A Y R S R V K F S R S A D A P

A Y Q Q G Q N Q L Y N E L N L G R R E E Y D V L D

K R R G R D P E Met G G K P R R K N P Q E G L Y N

E L Q K D K Met A E A Y S E I G Met K G E R R R G

K G H D G L Y Q G L S T A T K D T Y D A L H Met Q

A L P P R

Example 13

CD19-FLAG CAR-T Cells Expand >100 Fold In Vitro

Figure 3:
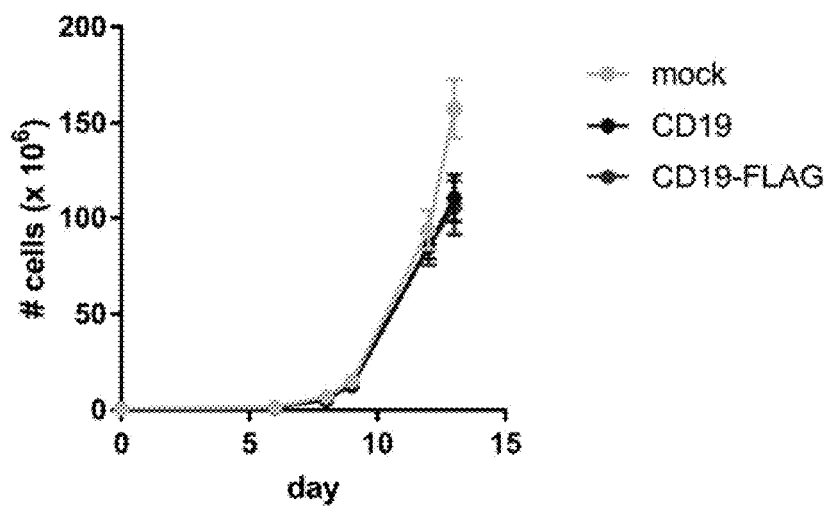
FIG. 3 shows that CD19-FLAG CAR-T cells exhibited comparable expansion to CD19 CAR-T cells. Mock CAR-T cells, CD19 CAR-T cells and CD19-FLAG CAR-T cells expanded >100-fold in vitro. A representative growth curve from three independent experiments is shown.
Figure 4:
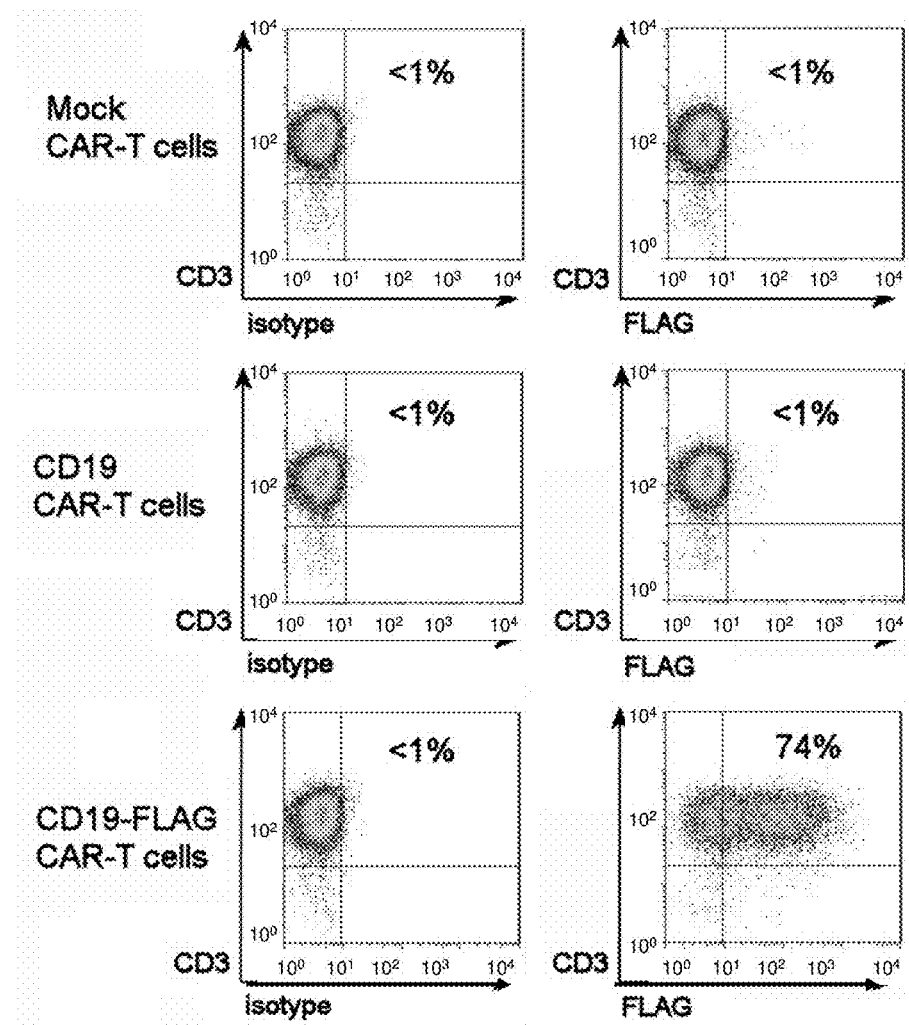
FIG. 4 shows that CD19-FLAG CAR-T cells exhibited high transduction efficiency. Mock CAR-T cells, CD19 CAR-T cells and CD19-FLAG CAR-T cells were stained by flow cytometry on day 8 of culture using an antibody against CD3 (Y-axis) and an antibody specific for the FLAG epitope (X-axis, right column) or its isotype control antibody (X-axis, left column).

Sequences for each CAR were transferred into a lentiviral vector downstream of the cytomegalovirus immediate-early promoter, and CAR-encoding lentivirus particles were produced by transient transfection of HEK293FT cells. The viruses were added at an MOI of 5 to activated human T cells, which were then cultured with IL-2 for 14 days. The CAR-T cells (mock, CD19, CD19-FLAG) expanded over 100-fold during this time (FIG. 3), indicating that the FLAG tag did not impact CAR-T cell expansion. Analysis of the cells by flow cytometry indicated that the transduction efficiency was >70% (FIG. 4). Thus, CD19-FLAG CAR-T expand in vitro similarly to CD19-CAR-T cells.

Example 14

CD19-FLAG CAR-T Cells Exhibit Strong CD19-Dependent Cytolytic Activity

Figure 5:
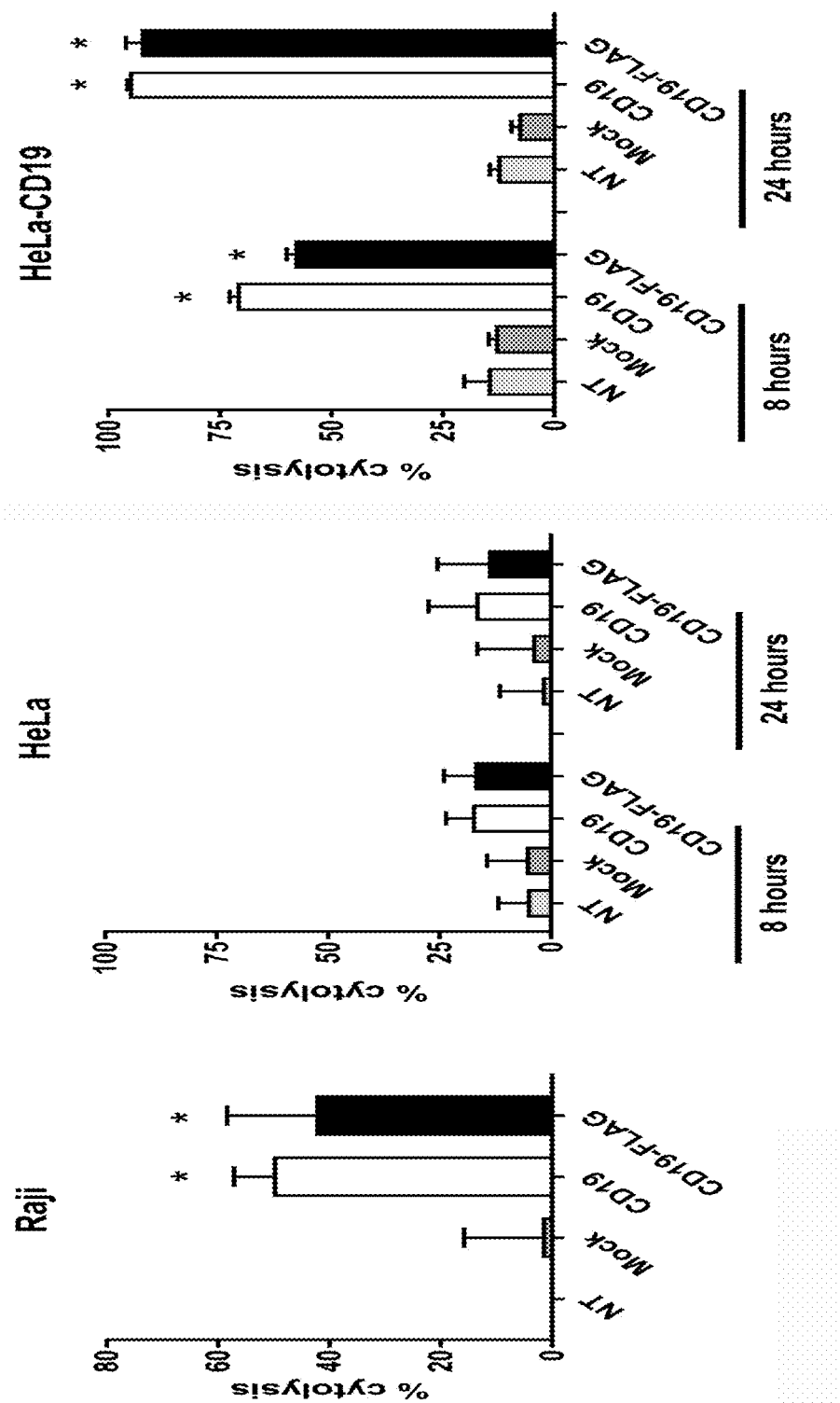
FIG. 5 shows that CD19-FLAG CAR-T cells are highly cytolytic for CD19+ cancer cells. The results show quantitation of cytolysis after T cell addition. Left panel, Raji cells, *: $p<0.05$ for CD19 or CD19-FLAG CAR-T cells compared to non-transduced T cells (NT) and to mock CAR-T cells. Right panel, HeLa-CD19 cells; *: $p<0.0001$ for CD19 or CD19-FLAG CAR-T cells compared to non-transduced T cells (NT) and to mock CAR-T cells. Middle panel: HeLa cells.

The ability of the CD19 and CD19-FLAG CAR-T cells to kill CD19-bearing target cells was tested using two human cell lines: the B cell line Raji, which endogenously expresses CD19, and the cervical carcinoma line HeLa which was engineered to overexpress CD19. Cytolysis was detected using the real-time cell analysis (RTCA) iCELLigence system, which measures the impedance of the target cell monolayer over time; as the target cells are killed by the effector cells, the impedance decreases. The CD19 and CD19-FLAG CAR-T cells exhibited significant cytolytic activity against both Raji cells (FIG. 5 left) and Hela-CD19+ cells (FIG. 5 right), but not against CD19$^-$ HeLa cells (FIG. 5 middle). In contrast, mock CAR-T cells and non-transduced T cells did not exhibit significant cytolytic activity against any of the target cells. Thus, both CD19 and CD19-FLAG CAR-T cells exhibited strong CD19-dependent cytolytic activity.

Example 15

Figure 6:
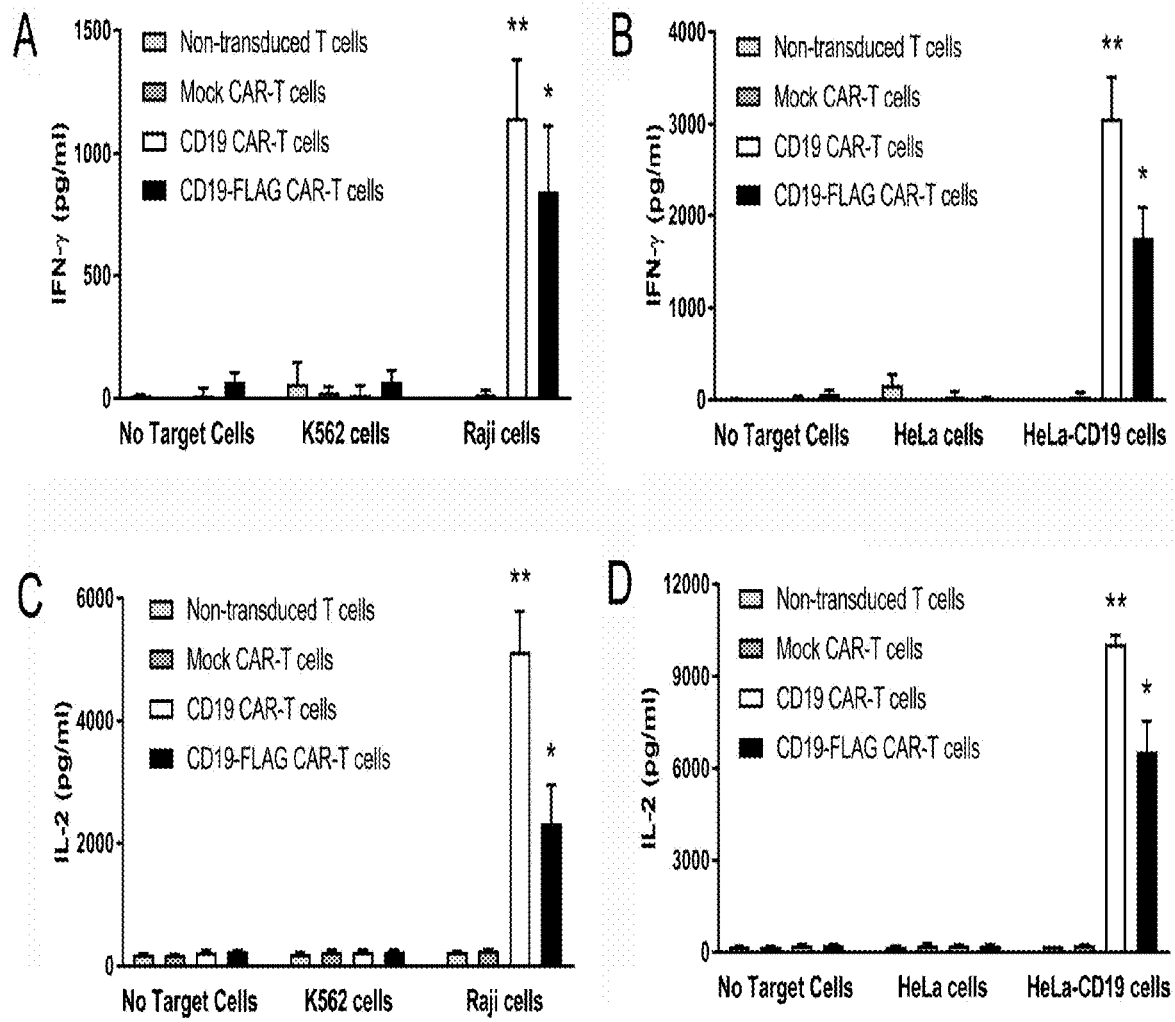
FIG. 6 shows that CD19-FLAG CAR-T cells produce moderated levels of IFN-γ and IL-2 in response to CD19+ cancer cells. A: IFN-γ production by non-transfected T cells, mock CAR-T cells, CD19 CAR-T cells or CD19-FLAG CAR-T cells after culture with endogenous CD19+ Raji cells or CD19− K562 cells; **$p=0.002$, *$p=0.008$ for Raji cells over K562 cells. B: IFN-γ production by the same cell preparations after culture with CD19-overexpressing HeLa-CD19 cells or CD19− HeLa cells. **$p<0.0001$, *$p=0.0003$ for HeLa-CD19 cells over HeLa cells. C: IL-2 production by the cell preparations after culture with endogenous CD19+ Raji cells or CD19− K562 cells; **$p<0.0001$, *$p=0.002$ for Raji cells over K562 cells. D: IL-2 production by the cell preparations after culture with CD19-overexpressing HeLa-CD19 cells or CD19− HeLa cells. **$p<0.0001$, *$p<0.0001$ for HeLa-CD19 cells over HeLa cells. All conditions were performed in triplicate.

CD19-FLAG CAR-T Cells Secrete Less IFN-γ, IL-2, and IL-6 in Response to CD19$^+$ Tumor Cells, Than CD19 CAR-T Cells The CAR-T cells were evaluated for their ability to produce IFN-γ and IL-2 in response to CD19$^+$ target cells. Both CD19 and CD19-FLAG CAR-T cells produced significantly higher levels of IFN-γ (FIG. 6 A-B) and IL-2 (FIG. 6 C-D) when cultured with CD19$^+$ target cells (Raji and HeLa-CD19) than when cultured with CD19$^-$ target cells (K562 and HeLa). Further, the CD19-FLAG CAR-T cells produced lower levels of IFN-γ and IL-2 than did the CD19 CAR-T cells. In contrast, the mock CAR-T cells and non-transduced T cells did not produce significant levels of either cytokine when cultured with any of the target cell lines. The results show that both CD19 and CD19-FLAG CAR-T cells secreted IFN-γ and IL-2 in a CD19-dependent manner, and CD19-FLAG CAR-T produced significantly less IFN-γ and IL-2 in CD19$^+$ cells than CD19 CAR-T produced.

Figure 7:
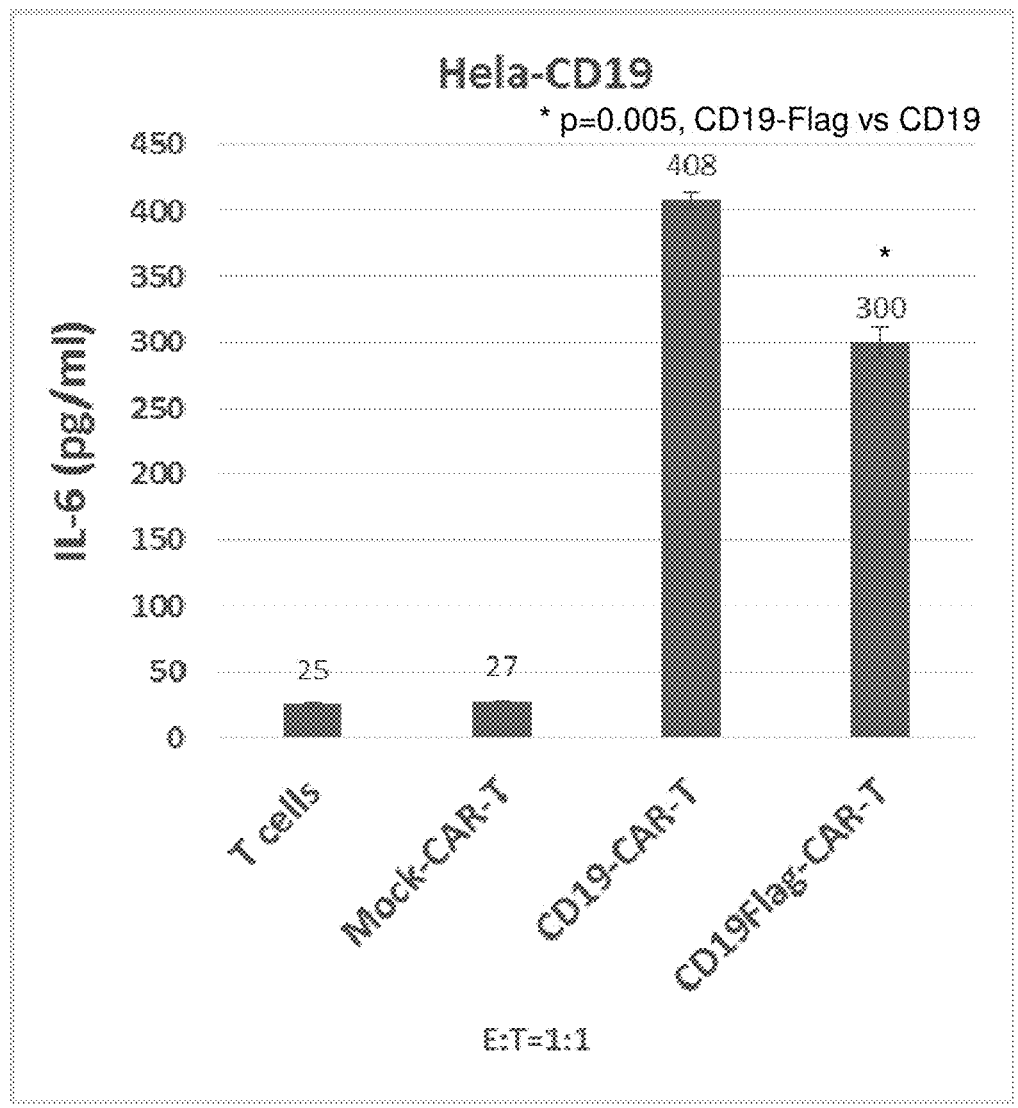
FIG. 7 shows reduced IL-6 secretion by CD19-FLAG-CAR-T cells versus CD19-CAR-T cells against Hela-CD19 target cells. *$p=0.005$

FIG. 7 shows reduced IL-6 secretion by CD19-FLAG-CAR-T cells versus CD19-CAR-T cells against Hela-CD19 target cells.

Example 16

CD19-FLAG CAR-T and CD19 CAR-T Cells Inhibit CD19$^+$ Solid Tumors In Vivo

To determine the effect of CD19 and CD19-FLAG CAR-T cells on solid tumors in vivo, we developed a novel xenograft tumor model using the HeLa-CD19 cell line. Immunodeficient NSG mice were injected subcutaneously on each flank with $2\times10^6$ HeLa-CD19 cells, and the sizes of the tumors were monitored for 36 days. The tumors injected with CD19 and CD19-FLAG CAR-T cells (average 285 mm$^3$) were significantly smaller than the control tumors injected with non-transduced T cells (average 935 mm$^3$).

Figure 8:
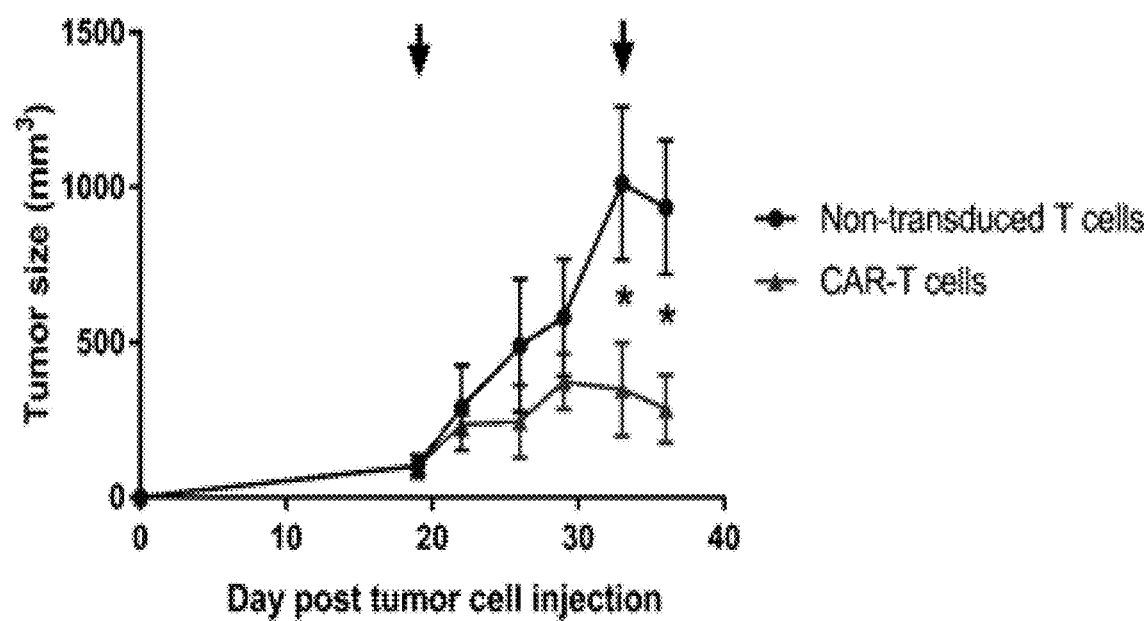
FIG. 8 shows intra-tumoral injections of CD19 on day 19 and CD19-FLAG CAR-T cells on day 33 significantly inhibited HeLa-CD19 tumor growth. *: $p<0.05$ for CAR-T cells compared to non-transduced T cells, determined by Student's t test assuming unequal variances.

FIG. 8 shows the average growth curves for the tumors treated with non-transduced T cells and the tumors treated with CD19 CAR-T cells on day 19 and CD19-FLAG CAR-T cells on day 33. The results show that intra-tumoral injections of CD19 and CD19-FLAG CAR-T cells significantly inhibited HeLa-CD19 tumor growth. *: p<0.05 for CAR-T cells compared to non-transduced T cells, determined by Student's t test assuming unequal variances.

Figure 9:
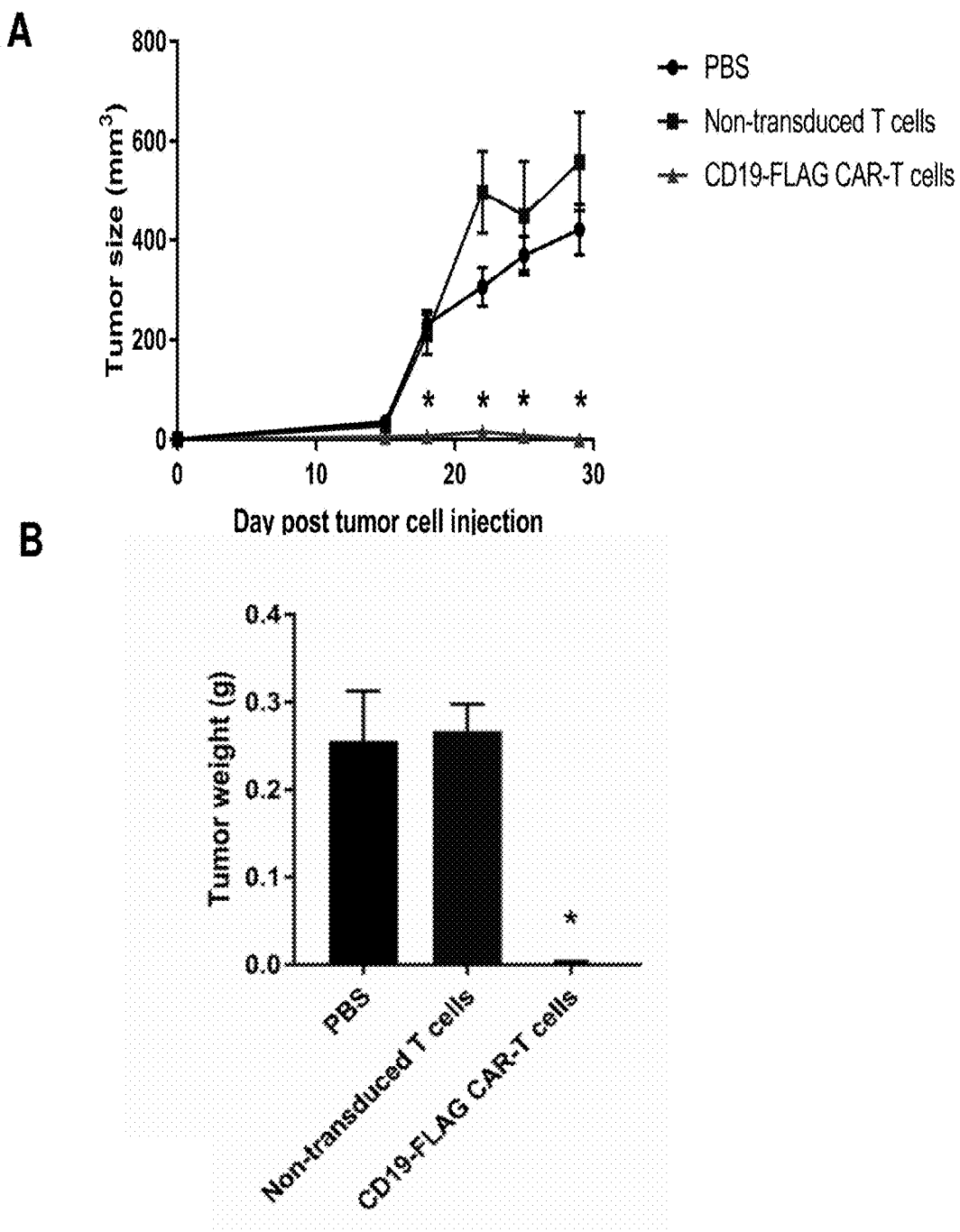
FIG. 9 shows intravenous injections of CD19-FLAG CAR-T cells significantly inhibited HeLa-CD19 tumor growth. A: Hela-CD19 xenograft tumor growth curves, averaged per group; *: p<0.005 for CD19-FLAG CAR-T cells compared to non-transduced T cells. B: average weights of the dissected xenograft tumors; *: p=0.002 CD19-FLAG CAR-T cells compared to non-transduced T cells.

To characterize the effect of CD19-FLAG CAR-T cells in the HeLa-CD19 solid tumor model, a second study was conducted with earlier, intravenous application of the CD19-FLAG CAR-T cells. In this study, the CD19-FLAG CAR-T cells almost completely blocked tumor growth (FIG. 9A-B), with no effect on mouse weight. In addition, immunohistochemical analysis of the CD19-FLAG group tumor demonstrated an increased amount of cleaved caspase-3 compared to tumors from the two control groups (data not shown), indicating induced apoptosis of the tumor cells.

Figure 10:
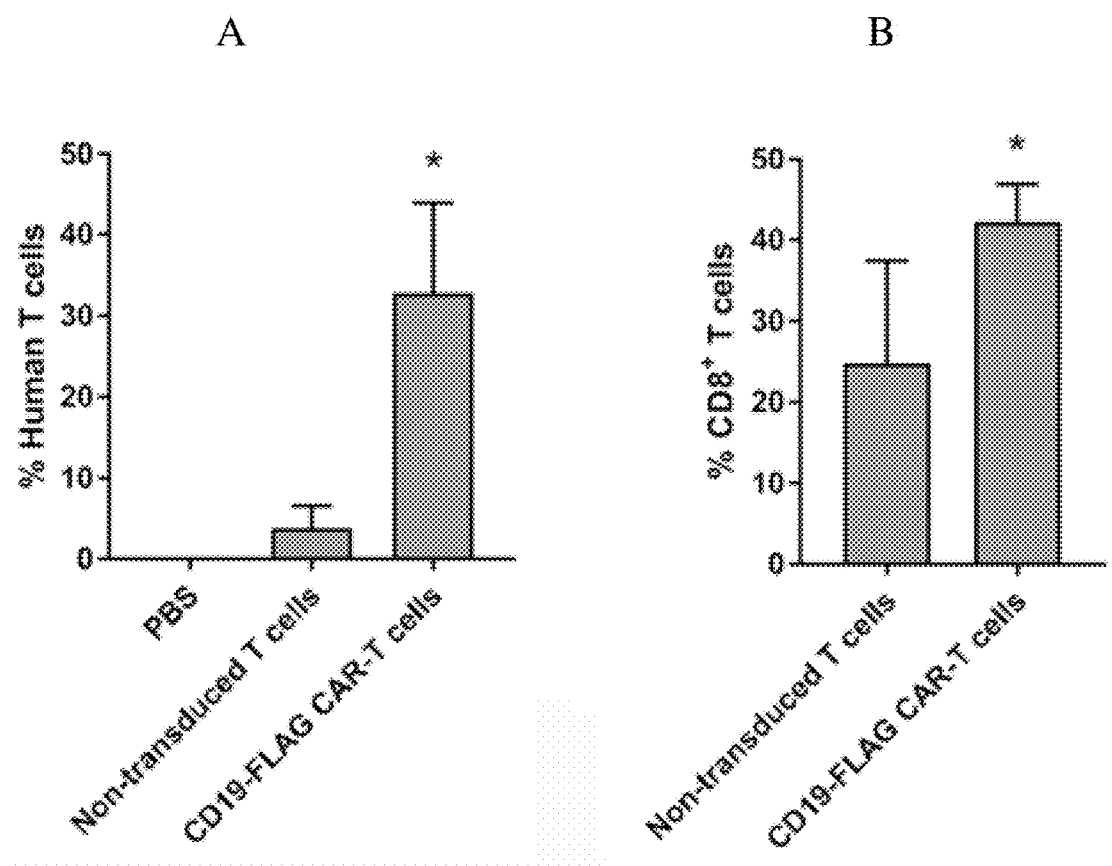
FIG. 10 shows HeLa-CD19 tumor-bearing mice treated with CD19-FLAG CAR-T cells contained increased numbers of human T cells in the peripheral blood. A: average frequency of human T cells among the peripheral blood leukocytes; *: p<0.0001 for CD19-FLAG CAR-T cells compared to non-transduced T cells. B: average frequency of CD8+ cells among the human T cells; *: p=0.02 for CD19-FLAG CAR-T cells compared to non-transduced T cells.

Moreover, at the end of the study, the frequency of human T cells in the peripheral blood was 32.8±4.9% in the CD19-FLAG group but only 3.8±1.2% in the non-transduced T cell group (FIG. 10A). Of the human T cells, the ratio of CD8$^+$ cells to CD8$^-$ cells was also higher in the CD19-FLAG group than the non-transduced T cell group (FIG. 10B). Thus, CD19-FLAG CAR-T cells not only significantly blocked solid tumor growth but also expanded in vivo to kill the cancer cells.

Example 17

CD19-FLAG CAR-T Cells Inhibit CD19+ Hematological Cancer In Vivo

Figure 11:
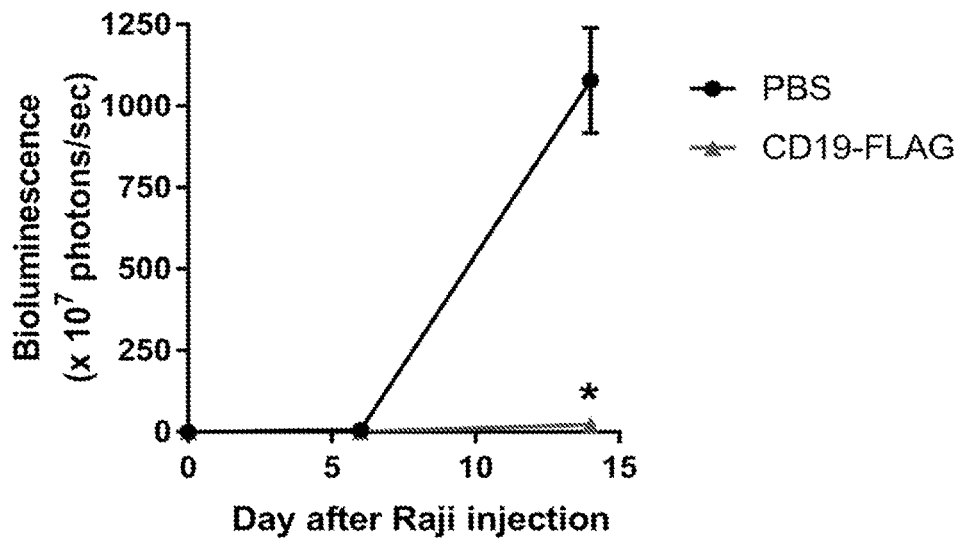
FIG. 11 shows CD19-FLAG CAR-T cells significantly block Raji xenograft tumor growth and prolong survival. A: quantitation of the imaging data. Mice treated with CD19-FLAG CAR-T cells, but not PBS-treated mice, were almost completely free of Raji cells at day 14; *: p=0.0002. Error bars represent standard errors of the means. B: Kaplan-Meier survival plot showing that CD19-FLAG CAR-T cells significantly prolonged survival of mice in the Raji xenograft model; *p=0.003.
Figure 11:
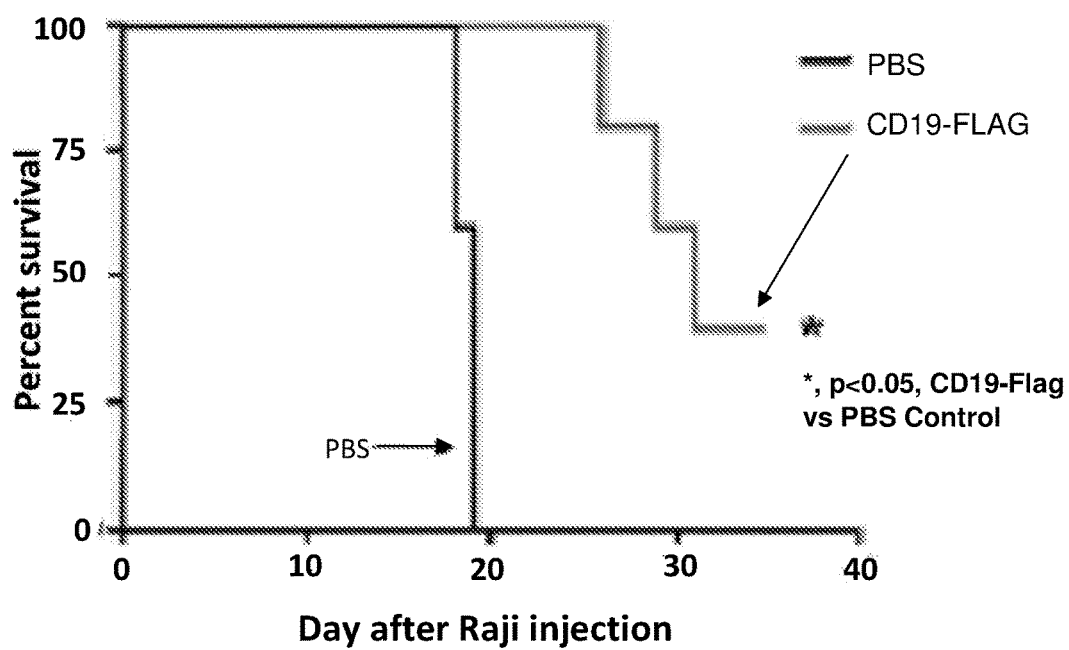

To analyze the effect of CD19-FLAG CAR-T cells on a hematological cancer in vivo, we injected NSG mice with luciferase+ Raji cells and used IVIS in vivo imaging. Compared to the PBS control, CD19-FLAG cells significantly decreased Raji tumor cell burden (FIG. 11A) and significantly ($p<0.05$) prolonged mouse survival (FIG. 11B). The effect was similar to CD19-CAR-T cells (not shown).

It is to be understood that the foregoing describes preferred embodiments of the present invention and that modifications may be made therein without departing from the scope of the present invention as set forth in the claims.

---

What is claimed is:

1. Chimeric antigen receptor (CAR)-T cells modified to express a CAR fusion protein comprising from N-terminus to C-terminus:
   (i) a single-chain variable fragment (scFv) comprising $V_H$ having the amino acid sequence of SEQ ID NO: 5 and $V_L$ having the amino acid sequence of SEQ ID NO: 3, wherein the scFv has an activity against a tumor antigen CD19,
   (ii) a transmembrane domain,
   (iii) at least one co-stimulatory domains, and
   (iv) an activating domain;
   wherein the fusion protein further comprises a FLAG tag N-terminus to the scFv, C-terminus to the scFv, or between $V_H$ and $V_L$.

2. The CAR-T cells according to claim 1, wherein the co-stimulatory domain is selected from the group consisting of CD28, 4-1BB, ICOS-1, CD27, OX-40, DAP10 and GITR.

3. The CAR-T cells according to claim 1, wherein the co-stimulatory domain is CD28.

4. The CAR-T cells according to claim 1, wherein the activating domain is CD3-zeta.

5. The CAR-T cells according to claim 1, wherein the CAR fusion protein has the amino acid sequence of SEQ ID NO: 10.

6. A CAR fusion protein comprising the amino acid sequence of SEQ ID NO: 10.

7. An adoptive cell therapy method for treating cancer, comprising the step of administering the CAR-T cells of claim 5 to a subject suffering from cancer, whereby the subject has reduced cytokine release caused by infused CAR T cells comparing with a subject administered with similar CAR-T cells but without a FLAG tag in CAR.

8. An adoptive cell therapy method for treating cancer, comprising the step of administering the CAR-T cells of claim 5 to a subject suffering from cancer, whereby the subject has reduced incidence of cytokine release syndrome comparing with a subject administered with similar CAR-T cells but without a FLAG tag in CAR.

* * * * *